United States Patent
Brunelle et al.

(12)

(10) Patent No.: US 6,559,333 B1
(45) Date of Patent: May 6, 2003

(54) METHOD FOR PURIFYING ALIPHATIC AMINONITRILES

(75) Inventors: Jean-Pierre Brunelle, Croissy-sur-Seine (FR); Philippe Leconte, Meyzieu (FR); Philippe Marion, Vernaison (FR)

(73) Assignee: Rhodia Fiber & Resin Intermediates, Courbevoie Cedex (FR)

( * ) Notice: Subject to any disclaimer, the term of this patent is extended or adjusted under 35 U.S.C. 154(b) by 0 days.

(21) Appl. No.: 09/673,299

(22) PCT Filed: Apr. 13, 1999

(86) PCT No.: PCT/FR99/00862

§ 371 (c)(1),
(2), (4) Date: Jan. 25, 2001

(87) PCT Pub. No.: WO99/54285

PCT Pub. Date: Oct. 28, 1999

(30) Foreign Application Priority Data

Apr. 16, 1998 (FR) .............................. 98 05044

(51) Int. Cl.[7] .............................. C07C 255/24
(52) U.S. Cl. .................. 558/459; 558/452; 558/454; 558/456
(58) Field of Search ................ 558/452, 454, 558/456, 459

(56) References Cited

U.S. PATENT DOCUMENTS

| 5,133,838 A | * | 7/1992 | Sieja ............................ 203/29 |
| 5,153,351 A | * | 10/1992 | Sieja ........................... 558/452 |
| 5,527,946 A | * | 6/1996 | Flick et al. ................. 558/459 |
| 6,153,748 A | * | 11/2000 | Fuchs et al. ................ 540/484 |

FOREIGN PATENT DOCUMENTS

| EP | 0 502439 A | 9/1992 |
| WO | 93 14064 A | 7/1993 |
| WO | 98 34899 A | 8/1998 |

* cited by examiner

Primary Examiner—Sreeni Padmanabhan
Assistant Examiner—Ebenezer Sackey
(74) Attorney, Agent, or Firm—Burns, Doane, Swecker & Mathis, L.L.P.

(57) ABSTRACT

The present invention relates to a process for the purification of aliphatic aminonitriles and more particularly of 6-aminocapronitrile.

It consists more specifically in subjecting 6-aminocapronitrile to a hydrogenation with molecular hydrogen in the presence of a catalyst comprising at least one metal chosen from palladium, platinum, ruthenium, osmium, iridium or rhodium and a promoter agent or a preconditioning in order to improve the selectivity of the hydrogenation.

18 Claims, No Drawings

METHOD FOR PURIFYING ALIPHATIC AMINONITRILES

This application is a 371 PCT/FR 99/00862 filed Apr. 13, 1999.

The present invention relates to a process for the purification of aliphatic aminonitriles and more particularly of 6-aminocapronitrile.

6-Aminocapronitrile is generally prepared by hydrogenation of one of the two nitrile functional groups of adiponitrile. Thus, U.S. Pat. No. 5,151,543 discloses a process for the partial hydrogenation of dinitriles to aminonitriles, in a solvent in molar excess of at least 2/1 with respect to the dinitrile comprising liquid ammonia or an alkanol comprising an inorganic base soluble in the said alkanol, in the presence of a catalyst of Raney nickel or cobalt type.

Patent WO-A-96/18603 discloses a process for the hemihydrogenation of aliphatic dinitriles to the corresponding aminonitriles using hydrogen and in the presence of a catalyst chosen from Raney nickel and Raney cobalt, the said Raney nickel or cobalt optionally comprising a doping element chosen from the elements from Groups IVb, VIb, VIIb and VIII of the Periodic Classification of the Elements and zinc, and of a strong inorganic base deriving from an alkali metal or alkaline earth metal, the starting hydrogenation medium comprising water, in a proportion of at least 0.5% by weight with respect to the combined liquid compounds in the said medium, diamine and/or aminonitrile, which can be formed from the dinitrile to be hydrogenated, as well as unconverted dinitrile, in a proportion for these three combined compounds of 80% to 99.5% by weight with respect to the combined liquid compounds in the said medium, the said process making it possible to obtain a selectivity for the targeted aminonitriles of at least 60%.

One of the possible uses of 6-aminocapronitrile (also known as ACN for convenience in the present text) consists in reacting it with water and in cyclizing it (cyclizing hydrolysis) in order to obtain caprolactam, which is the starting material for polyamide 6.

This cyclizing hydrolysis can be carried out in the liquid phase, as disclosed in Patent WO-A-96/00722, or in the vapour phase, as disclosed in Patent EP-A-0,659,741 or Patent WO-A-96/22974.

6-Aminocapronitrile subjected to cyclizing hydrolysis can contain up to several per cent of impurities, such as hexamethylenediamine or various imines formed during the hydrogenation of adiponitrile, without this prohibiting the said cyclizing hydrolysis reaction. This is particularly the case when the hydrolysis is carried out in the vapour phase. However, a portion of these impurities, converted or otherwise during the hydrolysis, may be reencountered in the caprolactam obtained. Now, even if the amounts of impurities which can be found in the caprolactam are relatively low, for example of the order of 1 to 2%, the purity required during the subsequent polymerization of the caprolactam is such that the purification of the said caprolactam can prove to be complex and very expensive. The purification of the 6-aminocapronitrile makes it possible to simplify the purification treatments of the caprolactam obtained. Thus, for example, the treatment of the caprolactam disclosed in patent WO-A-98/05636 can be carried out by passing over an ion-exchange resin and distillation, when the 6-aminocapronitrile is purified, and can additionally comprise a hydrogenation operation, if the 6-aminocapronitrile has not been sufficiently purified before its hydrolysis.

A purification of 6-aminocapronitrile before its conversion into caprolactam can consequently be regarded as technically and economically highly useful.

The present invention consists of a relatively simple process for the purification of aminonitrile, such as the purification of the 6-aminocapronitrile obtained after separation of the unconverted adiponitrile or directly by treatment of the reaction mixture from the hemihydrogenation of adiponitrile.

Hexamethylenediamine is coproduced with 6-aminocapronitrile during the hydrogenation of adiponitrile.

It can either be separated, completely or partially, from the said 6-aminocapronitrile before the treatment of the latter or, preferably, be kept in the mixture for the said treatment. In the present text, unless otherwise specified, the term 6-aminocapronitrile (or ACN) will therefore cover 6-aminocapro-nitrile and its mixtures with hexamethylenediamine. More generally, the term aminonitrile denotes, in the present text, a medium comprising an aminonitrile to be purified and optionally one or more diamines.

It consists more specifically in subjecting an aminonitrile and preferably 6-aminocapronitrile to a hydrogenation with molecular hydrogen in the presence of a catalyst comprising at least one metal chosen from palladium, platinum, ruthenium, osmium, iridium or rhodium.

The process of the invention applies more specifically to the purification of 6-aminocapronitrile and in particular of that obtained by hemihydrogenation of adiponitrile, such as that described in the preceding paragraph.

This catalyst comprises either one or more promoter elements generally chosen from Groups Ib, IIIa, IVa, Va, VIa, VIb and VIIb of the Periodic Classification of the Elements, such as published in the Handbook of Chemistry and Physics, 51st Edition (1970–1971) by The Chemical Rubber Company, or is subjected to a preconditioning stage which consists in bringing it into contact with a selectivating agent before or at the beginning of the hydrogenation reaction.

This preconditioning stage is optional when the is catalyst comprises, as catalytic element, an element chosen from the group consisting of ruthenium, osmium, iridium and rhodium, in the presence or otherwise of promoter elements.

In contrast, this stage is necessary when the catalyst comprises an element chosen from the group comprising palladium and platinum, in the absence of promoter elements.

Mention may be made, as examples of promoter elements suitable for the invention, of elements such as gold, silver, copper, chromium, molybdenum, tungsten, germanium, tin, lead, boron, gallium, indium, thallium, phosphorus, arsenic, antimony, bismuth, sulphur, selenium, tellurium, manganese, rhenium, vanadium, titanium or zinc.

These promoter elements can be in the free form or in the combined form, for example in the form of oxides or of salts. They have the aim of improving the selectivity of the hydrogenation of the impurities, in particular of the imines, by inhibiting even more the hydrogenation of the nitrile functional group of the aminonitrile and in particular of ACN. They are preferably employed with palladium, platinum and ruthenium catalysts. The promoter element/catalyst metal ratio by weight varies according to the promoter. It is generally between 0% and 100%. This ratio is preferably between 5 and 60% by weight for some promoters, such as silver. For other promoters, this ratio by weight varies between 0.0001% and 10%.

According to another characteristic of the invention, the catalyst of the invention can be subjected or is subject, according to its composition, to a preconditioning stage which makes it possible to improve the selectivity of the hydrogenation, that is to say to improve the degree of hydrogenation of the impurities of the aminonitrile, such as imines, while keeping the degree of hydrogenation of the aminonitrile at a minimum value.

This preconditioning stage consists in subjecting the catalyst to a fluid comprising a selectivating agent. This treatment can be carried out on the catalyst before it is charged to the hydrogenation reactor, by treatment with a flow of hydrogen comprising a certain amount of selectivating agent.

However, in a preferred embodiment of the invention, the preconditioning of the catalyst is carried out directly in the hydrogenation reactor, at the beginning of hydrogenation, either by feeding a flow of hydrogen comprising the said selectivating agent for a predetermined period of time sufficient to feed the desired amount of selectivating agent or by feeding the said selectivating agent as a mixture with the flow of aminonitrile to be hydrogenated for a period of time corresponding to feeding the desired amount of the said agent.

Of course, a selectivating agent can be present simultaneously in the flow of hydrogen and the aminonitrile to be treated, it being possible for this agent to be identical or different.

Mention may be made, by way of example, as selectivating agent suitable for the invention, of those belonging to the group comprising carbon monoxide, organic sulphur compounds and organic phosphorus compounds.

More specifically, the organic sulphur compounds can be chosen from the group comprising thiourea and its derivatives, thiols and alkyl sulphides and the organic phosphorus compounds from the group comprising phosphites, alkyl hypophosphites and alkyl phosphates and thiophosphates.

According to another characteristic of the invention, the amount of selectivating agent added per tonne of catalyst to be preconditioned (including support) is advantageously between 0.5 and 15 mol of selectivating agent per tonne of catalyst.

The hydrogenation process of the invention makes it possible to very significantly decrease the amount of impurities, in particular of imine type, present in the aminonitrile and in particular in 6-aminocapronitrile. The presence of such impurities is illustrated and expressed by a high polarographic index (this number is generally known by the abbreviation POLN). The presence of such impurities or the measurement of a high POLN would be reflected in particular by the appearance of a coloration and the formation of branchings during the polymerization of the caprolactam obtained by cyclization of the aminonitrile, if they were reencountered in the latter. Among these imines, tetrahydroazepine (THA) is one of the most well known and one of the most difficult to remove, in particular by distillation. In contrast, the hydrogenation carried out according to the process of the invention does not significantly affect the nitrile functional group of 6-aminocapronitrile.

The polarographic index, determined by polarography, is expressed in moles of imine functional group per tonne of sample to be quantitatively determined.

Various techniques have been provided for the removal of THA. Thus, Patent WO-A-93/14064 discloses the reaction of THA with a compound with an active methylene group, such as malonitrile or nitromethane, in order to obtain an addition compound of higher molecular mass which can be separated more easily from 6-aminocapronitrile. Such a technique involves the introduction of a new reactant, which further complicates the already complex treatments of 6-aminocapronitrile. In addition, the compounds used are relatively expensive and can, in some cases, be problematic to use (nitromethane or nitroethane, for example).

Patent EP-A-0,502,439 discloses the purification of 6-aminocapronitrile by reduction of tetrahydroazepine using a hydride, more particularly sodium borohydride, in an amount much greater than the stoichiometric amount, preferably 4 to 5 times the said stoichiometric amount. Such a process can hardly be envisaged on an industrial scale because of the very high costs of such hydrides. In addition, the presence of hydride can complicate the subsequent treatment of 6-aminocapronitrile.

The hydrogenation is a simple operation which proves to be highly efficient. It can be carried out according to the usual techniques. The hydrogenation can in particular be carried out with a catalyst deposited as a stationary bed, with which the ACN to be treated and the hydrogen are brought into contact.

The hydrogenation can also be carried out with a catalyst suspended in the reaction mixture by stirring.

The catalyst employed generally comprises the active metal finely divided and deposited on a solid support. Mention may be made, as support, without implied limitation, of oxides, such as alumina, zirconia, titanium dioxide or silica, or alternatively active charcoals.

Preference is given, among the catalysts employed in the present process, to those which comprise at least palladium, which catalysts prove to be particularly efficient.

The hydrogenation is carried out at a temperature compatible with the stability of the aminonitrile and more particularly of ACN, on the one hand, and which makes it possible to have satisfactory kinetics, on the other hand. A temperature of between 20° C. and 150° C. is usually suitable.

The hydrogenation will preferably be carried out at the lowest possible temperature compatible with the kinetics objective.

The absolute hydrogen pressure at the hydrogenation temperature can vary within wide limits. It is generally between 1 bar and 100 bar but is preferably between 2 and 50 bar.

It is not necessary to dilute the aminonitrile, for example ACN, in a solvent in order to subject it to the hydrogenation operation. However, the present invention can be carried out in the presence of variable amounts of solvent. The solvent which can be used must then be inert with respect to the aminonitrile (ACN) and hydrogen. Mention may be made, as non-limiting examples of such solvents, of water and ammonia. The amount of water can vary within large proportions; it preferably represents from 0% to 40% by weight of the weight of ACN to be treated and more preferably from 0% to 30%. The ammonia can be used in even more variable amounts, for example between 0% and 100% by weight of the weight of ACN. The presence of water and of ammonia can also be envisaged in the process of the invention.

The hydrogenation is advantageously followed by a distillation which makes it possible to separate the ACN from the hydrogenated impurities, in particular from imines converted into amines, as well as from the hexamethylenediamine which it may comprise. This distillation is carried out according to the usual techniques.

The purified ACN is subjected to a cyclizing hydrolysis, by reaction with water, resulting in the formation of caprolactam. This cyclizing hydrolysis is carried out in a known way, either in the vapour phase or in the liquid phase.

The examples given below solely by way of indication illustrate the invention.

COMPARATIVE EXAMPLE 1

80 g of a catalyst composed of metallic Pd deposited on an alumina support (0.3% by weight of Pd) are placed as a stationary bed in a reactor.

The reaction is carried out at 80° C. and under a hydrogen pressure (under warm conditions) of 20 bar.

The 6-aminocapronitrile employed exhibits an initial polarographic index (POLN) of 84 mol/t. 350 g of this ACN are introduced, hydrogenation being carried out in 2 h 30 over the catalytic bed.

The variation in the POLN number and the degree of conversion of the aminonitrile, or more specifically the loss of aminonitrile due to the hydrogenation of the latter, are determined.

The latter value is determined by vapour phase chromatographic analysis.

The results obtained are collated in Table I below.

COMPARATIVE EXAMPLE 2

99 g of a catalyst composed of metallic Pd deposited on an active charcoal support (0.5% by weight of Pd) are placed as a stationary bed in a reactor.

The reaction is carried out at 80° C. and under a hydrogen pressure (under warm conditions) of 20 bar.

The 6-aminocapronitrile employed exhibits an initial polarographic index (POLN) of 92 mol/t. 278 g of this ACN are introduced in 3 h over the catalytic bed.

The results obtained are collated in Table I below.

COMPARATIVE EXAMPLE 3

140 g of a catalyst composed of metallic Ni deposited on a silica support (56% by weight of Ni) are placed as a stationary bed in a reactor.

The reaction is carried out at 80° C. and under a hydrogen pressure (under warm conditions) of 20 bar.

The 6-aminocapronitrile employed exhibits an initial polarographic index (POLN) of 92 mol/t. 299 g of this ACN are introduced in 3 h over the catalytic bed.

Polarographic analysis of the treated ACN shows a POLN value of 380 mol/t and therefore markedly higher than before treatment.

EXAMPLE 4

140 g of a catalyst composed of Pd and of Ag deposited on an alumina support (0.2% by weight of Pd, 0.1% by weight of Ag) are placed as a stationary bed in a reactor.

This catalyst is sold by the company Procatalyse under the name LD 271.

The reaction is carried out at 30° C. and under a hydrogen pressure (under warm conditions) of 5 bar.

The 6-aminocapronitrile employed exhibits an initial polarographic index (POLN) of 92 mol/t. 299 g of this ACN are introduced in 3 h over the catalytic bed.

The results obtained are collated in Table I below.

EXAMPLE 5

140 g of a catalyst composed of Pd and of Au deposited on an alumina support (0.2% by weight of Pd and 0.1% by weight of Au) are placed as a stationary bed in a reactor. This catalyst is sold by the company Procatalyse under the name LD 277.

The reaction is carried out at 30° C. and under a hydrogen pressure (under warm conditions) of 5 bar.

The 6-aminocapronitrile employed exhibits an initial polarographic index (POLN) of 92 mol/t. 299 g of this ACN are introduced in 3 h over the catalytic bed.

The results obtained are collated in Table I below.

EXAMPLE 6

Example 1 is repeated but with introduction of carbon monoxide in the hydrogen flow at the beginning of the reaction. 0.2 mmol of CO are thus introduced, that is to say 2.5 mol of CO/t of catalyst.

The hydrogenation is carried out with 300 g of ACN in 3 hours.

After 3 h, the polarographic index is 20 mol/t, the initial number being 92 mol/t.

EXAMPLE 7

Example 4 is repeated by using 10% by weight of water as solvent. The duration of the hydrogenation is 3 hours.

| Example | Catalyst | Temperature in ° C. | Pressure in bar | Loss of ACN as weight % of ACN charged | POLN, Start/Finish |
|---|---|---|---|---|---|
| 1, comparative | Pd/Al$_2$O$_3$ | 80 | 20 | 11 | 77/24 |
| 2, comparative | Pd/Al$_2$O$_3$ | 80 | 20 | 10 | 96/16 |
| 4 | Pd-Ag/Al$_2$O$_3$ | 40 | 5 | 0.4 | 92/18 |
| 5 | Pd/Au/Al$_2$O$_3$ | 30 | 5 | 1.6 | 92/58 |
| 6 | Catalyst Ex. 1, preconditioned | 80 | 20 | 1.6 | 92/20 |
| 7 | Catalyst Ex. 4 with 10% water | 40 | 5 | 0.2 | 90/16 |

What is claimed is:

1. A process for the purification of aminonitrile, comprising subjecting aminonitrile to hydrogenation with molecular hydrogen in the presence of a catalyst comprising at least one metal selected from the group consisting of palladium, platinum, ruthenium, osmium, iridium and rhodium, and wherein said catalyst comprises one or more promoter elements selected from the group consisting of gold, silver, copper, chromium, molybdenum, tungsten, germanium, tin, lead, boron, gallium, indium, thallium, phosphorus, arsenic, antimony, bismuth, sulphur, selenium, tellurium, manganese, rhenium, vanadium, titanium and zinc or said catalyst is subjected to a preconditioning stage which comprises bringing the catalyst into contact with a selectivating agent before or at the beginning of the hydrogenation reaction.

2. The process for the purification of aminonitrile, wherein the aminonitrile is subjected to hydrogenation with molecular hydrogen in the presence of a catalyst comprising at least one metal selected from the group consisting of ruthenium, osmium, iridium and rhodium.

3. The process according to claim 1, wherein the aminonitrile is 6-aminocapronitrile.

4. The process according to claim 1, wherein the catalyst comprises at least palladium.

5. The process according to claim 1, which is carried out at a temperature of between 20° C. and 150° C.

6. The process according to claim 1, which is carried out under an absolute hydrogen pressure at the hydrogenation temperature lying between 1 bar and 100 bar.

7. The process according to claim 1, wherein the catalyst employed comprises the active metal finely divided and deposited on a solid support.

8. The process according to claim 7, wherein the support of the catalyst is selected from the group consisting of alumina, zirconia, titanium dioxide, silica and active charcoal.

9. Process according to claim 2, wherein the catalyst additionally comprises one or more promoter elements.

10. Process according to claim 2, wherein the catalyst is subjected to a preconditioning stage which comprises bringing the catalyst into contact with a selectivating agent before or at the beginning of the hydrogenation reaction.

11. Process according to claim 1, wherein the promoter element/catalyst metal ratio by weight is between 0% and 100%.

12. Process according to claim 1, wherein the process for preconditioning the catalyst comprises introducing into the hydrogenation reactor comprising the catalyst, at the beginning of the hydrogenation reaction, a selectivating agent as a mixture either with the hydrogen or with the aminonitrile to be purified.

13. Process according to claim 1, wherein the selectivating agent is chosen from the group comprising carbon monoxide, organic sulphur compounds or organic phosphorus compounds.

14. Process according to claim 13, wherein the organic sulphur compounds are chosen from the group comprising thiourea, thiols or alkyl sulphides, the organic phosphorus compounds being chosen from the group comprising phosphites, alkyl hypophosphites, alkyl phosphates or thiophosphates.

15. Process according to claim 1, wherein the amount of selectivating agent added per tonne of catalyst to be preconditioned is between 0.5 and 15 mol of selectivating agent per tonne of catalyst.

16. Process according to claim 1, wherein the hydrogenation is followed by a distillation.

17. Process according to claim 11, wherein the promoter element/catalyst metal ratio by weight is between 5 and 60%.

18. Process according to claim 6, wherein the hydrogenation temperature lies between 2 bar and 50 bar.

* * * * *